United States Patent [19]

Hoerrmann

[11] Patent Number: 5,534,553
[45] Date of Patent: Jul. 9, 1996

[54] DRUG CONTAINING FATTY AMINO ALCOHOLS OR DERIVATIVES THEREOF

[76] Inventor: Wilhelm Hoerrmann, Staltacherstr. 34, D. 82393 Iffeldorf, Germany

[21] Appl. No.: 206,336

[22] Filed: Mar. 7, 1994

Related U.S. Application Data

[63] Continuation-in-part of Ser. No. 7,271, Jan. 21, 1993, abandoned, which is a continuation-in-part of Ser. No. 725,638, Jul. 3, 1991, abandoned, which is a continuation-in-part of Ser. No. 480,311, Feb. 15, 1990, abandoned, which is a continuation-in-part of Ser. No. 309,136, Feb. 13, 1989, abandoned, which is a continuation-in-part of Ser. No. 62,683, Jun. 16, 1987, abandoned.

[30] Foreign Application Priority Data

Jun. 12, 1987 [DE] Germany .......................... 37 1 9720.7

[51] Int. Cl.⁶ ..................................... A61K 31/13
[52] U.S. Cl. ........................................... 514/669
[58] Field of Search ..................... 514/625, 629, 514/669, 910, 911, 912, 913

[56] References Cited

U.S. PATENT DOCUMENTS

| | | | |
|---|---|---|---|
| 4,689,347 | 8/1987 | Dinu et al. ................................ | 514/562 |
| 4,859,769 | 8/1989 | Karlsson et al. ......................... | 514/625 |
| 4,897,382 | 1/1990 | della Valle et al. ..................... | 514/625 |
| 4,902,676 | 2/1990 | Peck et al. ............................... | 514/625 |

OTHER PUBLICATIONS

Chem. Abstracts 89(15):126105u Cardellina et al (1978).
Chem. Abstracts 72(23):117694 Klenk et al. (1970).
Hannun et al., *Science*, vol. 235 (Feb. 1987) pp. 670–674.
The Merck Manual, 14th edition (1982) pp. 1412–1432.

*Primary Examiner*—Raymond Henley, III

[57] ABSTRACT

This invention relates to the use of fatty amino alcohols or derivatives thereof as drugs for the consequences of drug dependency.

1 Claim, No Drawings

DRUG CONTAINING FATTY AMINO ALCOHOLS OR DERIVATIVES THEREOF

This application is a Continuation-in-part of application Ser. No. 08/007,271 filed Jan. 21, 1993 now abandoned, which is a continuation in part of Ser. No. 07/725,638 filed Jul. 3, 1991 now abandoned, which is a continuation in part of Ser. No. 07/480,311 filed Feb. 15, 1990, now abandoned, which is a continuation in part of Ser. No. 07/309,136 filed Feb. 13, 1989 now abandoned, which is a continuation in part of Ser. No. 07/062,683 filed Jun. 16, 1987 now abandoned.

The invention relates to a drug containing, by way of active substance, at least one isomer of a fatty amino alcohol or of its pharmaceutically acceptable derivatives, if necessary together with usual carriers and/or adjuvants.

Important among such fatty amino alcohols is sphingosine, i.e. 2-amino-4-octadecene-1,3-diol.

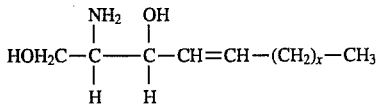

x = an integer of 12 or more

More specifically, it must be taken into account that said fatty aminoalcohols may exist in numerous isomeric forms. Since, with sphingosine, both carbon atom no. 2 and carbon atom no. 3, bearing either an amino or a hydroxyl group, are asymmetrical, there will be no less than 4 optical isomers. Owing to the double bond present, they can be combined with 2 geometric isomers, so that there is a total of 8 sphingosine isomers.

One among said isomers is trans-d-erythro-2-amino-4-octadecene-1,3-diol.

The drugs according to the invention may contain fatty amino alcohols, including sphingosine, in the form of pharmaceutically acceptable derivatives. These include, more particularly, ethers, esters, amides, salts and acid addition salts of the compounds named. Typical examples are N-acyl-derivatives containing saturated or unsaturated fatty acids, also called ceramides. Ceramides are an acid-amid-combination of saturated or unsaturated fatty acids of various chain length—especially lignoceric, cerebronic, nervonic, hydroxy-nervonic acids—and of a saturated or unsaturated fatty amino alcohol.

Ceramides united with phosphoryl-compounds such as phosphorylcholine are called sphingomyelins.

Ceramides united with sugar molecules or complex carbohydrate moieties are called cerebrosides, gangliosides or glycosphingolipids.

The central molecule of glycosphingolipids and sphingomyelines is sphingosine or ceramide respectively their function being to anchor the total molecular complex on to the cellular membrane. Any defects in sphingosine and/or ceramide molecular structures will entail serious consequences for the corresponding cellular membrane and its adnexa.

Main fields of application for this remedy are acquired immunodeficiency syndrome, drug dependence, and to some extent haemophilia.

Based on his studies, the applicant concluded that in all these diseases, including but not limited to AIDS, structural and functional disturbances of endogenous glycosphingolipids and sphingomyelines are of outstanding importance whereby however the lipid anchoring component is the decisive factor.

Applicants invention is therefore not directed to glycosphingolipids themselves, which are due to the antigenic properties of the carbohydrate moiety potentially dangerous substances. It is rather directed to the use of one or more fatty amino alcohol or its physiologically acceptable, functionally equivalent derivatives thereof.

Sphingosine and sphingosine-compound disturbances constitute, at least for some of the cases mentioned, a biochemical predisposition for acquiring the diseases mentioned.

The drug according to the invention can be used both to improve those suffering from damage due to such predisposition ("risk groups") and to treat clinically manifest diseases.

Chemically, the compounds named are known and, as such, can be produced by known chemical processes. This applies likewise to isomer separation.

It is novel, however, to use said substances in diseases such as AIDS, drug dependence, haemophilia and affections of the nervous system, especially when they are combined with the named disorders.

Adminstration can be performed orally, anally and parenterally. The compounds may be dissolved in vegetable oils, included in capsules or suppositories or added to emulsions. Liposomes techniques may also be used. Daily dosage is approximately 100–400 mg/kg body weight, the lower values preferably for parenteral, the higher values for oral-enteral application. It is the main purpose of this invention to restore as far as possible normal conditions of cell membranes as far as ceramides components are concerned. Dosage levels are more dependent on the extent of cell membrane damage than on the cause of the damage. As in many cases of everyday medical practice it is therefore the physicians task to decide the appropriate dosage within certain limits given. That is especially true where there is a combination with other known pharmaceutical agents. Such combination is above all to be expected in cases of aids as an adjuvant therapy. The duration of treatment is determined by the severity of symptoms and/or the danger of relapse.

Dosage levels refer to the content of sphingosine, generally of fatty amino alcohol content.

In spite of the fact that this application has a superficial similiarity with the invention of Karlsson et al (U.S. Pat. No. 4,859,769) this invention is fundamentally different of the Karlsson one. As a second step virus receptor the Karlsson invention is necessarily based on the carbohydrate moieties of sphingolipids. In contrast to that the essential factors of this invention are the anchoring and restoring properties of the lipid compounds fatty amino alcohols and ceramides in the cell membrane. So the intentions and methods alike are completely different in both inventions.

This invention can of course not mitigate all consquences of drug dependency. So viral hepatits cannot improved this way as this complication is less the direct effect of the drug as of infected injection needles and the like. This invention is directed to that complications of drug dependency which lead to damage of the cell membranes and especially of the lipid moieties of that membranes. Such damage can diagnostically be demonstrated for example in the cell membranes of epithelial and blood cells by biochemical analysis.

I claim:

1. A method for alleviating the structural and functional disturbances of endogenous glycosphingolipids and sphingomyelines in a patient suffering from a drug dependency which comprises administering to said patient one or more fatty-amino-alcohols or physiologically acceptable, functionally equivalent derivatives thereof in an amount of approximately 100–400 mg/kg bodyweight daily.

* * * * *